(12) United States Patent
Banham et al.

(10) Patent No.: US 6,780,224 B1
(45) Date of Patent: Aug. 24, 2004

(54) METHOD AND APPARATUS FOR ANTI-MICROBIAL AND RELATED TREATMENTS

(75) Inventors: Harry Banham, Bromley (GB); David Webber, Bromley (GB)

(73) Assignee: Universal Master Products Limited, Bromley (GB)

( * ) Notice: Subject to any disclaimer, the term of this patent is extended or adjusted under 35 U.S.C. 154(b) by 33 days.

(21) Appl. No.: 10/148,049

(22) PCT Filed: Nov. 24, 2000

(86) PCT No.: PCT/GB00/04479

§ 371 (c)(1),
(2), (4) Date: May 24, 2002

(87) PCT Pub. No.: WO01/37885

PCT Pub. Date: May 31, 2001

(30) Foreign Application Priority Data

Nov. 24, 1999 (GB) .............................. 9927617

(51) Int. Cl.$^7$ ................................................ B01D 5/00
(52) U.S. Cl. ............................ 95/273; 261/30; 261/107; 427/255.25; 165/133
(58) Field of Search ..................... 96/223, 226, 227, 96/222; 95/273, 285, 288; 261/30, 107; 427/25.25; 428/143; 165/133

(56) References Cited

U.S. PATENT DOCUMENTS

| | | | | |
|---|---|---|---|---|
| 3,017,239 A | * | 1/1962 | Rodman | ...................... 96/226 |
| 3,577,710 A | | 5/1971 | Feldman | |
| 4,200,442 A | | 4/1980 | Willot | |
| 4,295,343 A | | 10/1981 | Izumi | |
| 4,410,339 A | | 10/1983 | Bachhofer et al. | |
| 4,780,333 A | * | 10/1988 | Smith et al. | ................. 427/236 |
| 5,006,267 A | * | 4/1991 | Vaughn et al. | .............. 210/755 |
| 5,756,047 A | | 5/1998 | West et al. | |
| 5,911,742 A | | 6/1999 | Akazawa | |

FOREIGN PATENT DOCUMENTS

| | | |
|---|---|---|
| EP | 0267697 | 5/1988 |
| EP | 0274831 A2 | 7/1988 |
| GB | 456771 | 11/1936 |
| JP | 57175835 | 10/1982 |
| JP | 57179522 | 11/1982 |
| JP | 63075430 | 4/1988 |
| JP | 63108138 | 5/1988 |
| JP | 08094166 | 4/1996 |
| JP | 09173762 | 7/1997 |
| WO | WO 88/10122 | 12/1988 |

* cited by examiner

Primary Examiner—Robert A. Hopkins
(74) Attorney, Agent, or Firm—Richard M. Goldberg

(57) ABSTRACT

Method and apparatus for treatment of air conditioning systems and the like provides an air treatment element (18) comprising a microbial control medium and an entrainment medium therefor. The air treatment element (18) is adapted to be placed on the upstream side of the air cooling element (14) of an air conditioning system so that the air stream (16) thereto has entrained therein droplets of entrainment medium (32) containing the microbial treatment medium which are then condensed on the cooling surfaces, thereby removed from the air stream (16) and effectively applied to all relevant surfaces for exerting an effective microbial control action.

5 Claims, 3 Drawing Sheets

METHOD AND APPARATUS FOR ANTI-MICROBIAL AND RELATED TREATMENTS

BACKGROUND OF THE INVENTION

This invention relates to a method and apparatus for anti-microbial and related treatments. An example of the application of the invention is two systems for treating air conditioning systems with anti-microbial agents. Aspects of the invention are also applicable to systems for treatment of other equipment with anti-microbial and other agents, including for example the use of deodorant compositions and the like.

It is well known that there is a long standing requirement for systems for treating air conditioning systems in order to reduce the occurrence of such conditions as sick building syndrome and the like. Many proposals have been made. To the best of the applicants' knowledge, no currently available system offers the combination of effective microbial control with at least moderate ease of use and an acceptable price.

One of the difficulties arising in the case of the treatment of air conditioning systems is that the hardware includes ducting and passages with heat exchange surfaces and other intricate structures which all need effective treatment in order to reduce the opportunity for microbial growth at times when conditions favour such growth. The use of simple systems for mechanical cleaning are rendered more or less impossible by the complexity of the structures and the inaccessibility of the interstices of the system.

An important aspect of the difficulties inherent in designing a system for effective treatment of air conditioning systems is the fact that many, if not all, microbial control reagents have the usage requirement attached to them that the user must not allow the reagent to become dispersed unacceptably within the breathable environment encountered by users of the building. In other words, the treatment system needs to be confined to the actual air treatment equipment itself so that the latter is clean and the microbial presence acceptably reduced while the remainder of the building is unaffected by the microbial treatment material in any direct way.

Accordingly, there is considerable difficulty in providing a system which is easy to use, cost-effective and does not contravene regulations relating to the use of microbial treatment agents.

SUMMARY OF THE INVENTION

With this requirement in mind, the embodiments of the present invention are based upon the discovery disclosed below, and there is provided according to the invention the method and apparatus defined in the accompanying claims.

In the embodiments of the invention described below there is provided a system in which provision is made for treatment of substantially the entire relevant air-contacting surfaces of the air conditioning equipment. Such treatment occurs over a significant period, for example from one to 24 hours, depending upon the parameters of the installed treatment element and on the extent of use of the air conditioning equipment. The treatment system is effective to limit the application of the microbial treatment material to just those relevant surfaces of the air conditioning plant. Moreover, this limitation of the treatment of the surfaces of the air conditioning plant alone, without affecting the remainder of the building, is effected by that equipment itself and without the need to instal any additional equipment to achieve this result.

Moreover, in the embodiments, the treatment process is effective for a defined period of time (dependent upon the factors mentioned above) and then ceases, substantially automatically, so that the operation is effective in a time-limited way and lends itself to repetitive use at suitably-chosen intervals in order to maintain a satisfactorily level of microbial removal.

In the embodiments of the invention the method and apparatus is based upon our discovery that the treatment of the relevant surfaces of the air conditioning plant and equipment can be effectively achieved by means of a system in which a biocide material is provided and is made available in association with a carrier medium, for example water, but other fluids may be feasible for certain applications, and the biocide or microbial treatment material is entrained from an air treatment element so as to be carried in the air and air stream entering the air conditioning plant and is thus dispersed by the air flow-producing systems (for example a fan), so as to become reasonably uniformly distributed around the entire air-flow paths of the apparatus.

Thus, in this way, the entrained biocide material and its carrier medium, for example water droplets, are dispersed around the system and thus are available for treatment of all the relevant hardware surfaces.

In accordance with another important aspect of the present invention, the system furthermore operates in accordance with the following. After the entrainment of the microbial treatment material and its dispersal with the entrainment medium and the air currents around the system, there is provided the means for effectively removing the treatment medium for the air, and this provided by the refrigerated or cooled surfaces of the air conditioning plant. Thus, the air conditioning plant itself serves to remove the biocide or microbial treatment medium from the air flow around the hardware, and it does this by effectively condensing the carrier medium, usually water, so that its associated biocide material is likewise condensed on the relevant cooled surfaces. Effectively, this means that all such surfaces become coated with droplets of water vapour containing or carrying the biocide material with the result that all such surfaces are very effectively treated with the biocide.

Thus, in the embodiments of the invention, the system utilises symbiotically and beneficially, purely the existing hardware apparatus of the air conditioning plant firstly to cause the biocide material to be entrained with its carrier medium into the air flow and thus to be widely dispersed, and secondly the air conditioning plant is caused to remove the entrained treatment material and carrier medium for a condensation step.

Accordingly, it can now be seen that the system of the present invention makes effective and convenient use of existing hardware systems and employs these to achieve not only effective dispersal of relatively small quantities of biocide material about the system, but also achieves likewise the effective removal of the treatment material or medium from the system by a condensation step. In this way, the embodiments of the present invention are able to achieve the indicated requirements of such a system, without the need to employ any additional hardware and by means which involves the employment merely of air treatment elements comprising sachets of the treatment medium and the carrier medium.

It will be understood that the embodiments of the invention do rely on the use of a carrier medium for the biocide material which is capable of being removed by condensation at the temperature occurring in the relevant surfaces of the air conditioning hardware. In most cases the carrier medium will be water. Care also needs to be exercised in order to ensure that the air conditioning plant is arranged to operate the air flow-producing fan, which causes entrainment of the biocide material, with the carrier medium, only when the air conditioning plant is operating and the refrigerated surfaces, which effect condensation of the biocide and carrier medium, are at their relevant refrigeration temperatures.

In other embodiments of the invention, the air treatment elements may be used in alternative systems in which the combination of a biocide or microbial treatment material and a carrier medium are also of benefit. For example, there may be provided light weight air conditioning or air treatment apparatus for use in relation to transport boxes for placement in lorries and trucks. Such equipment employs the air treatment elements described above in relation to air conditioning plant, in combination with an air dispersal system not incorporating any refrigerated surfaces as such.

Such an arrangement is of utility and convenience in relation to the road and rail transport of refrigerated goods in which the-dispersal of biocide-containing air around the stored goods is of benefit and the requirement for healthy breathability of the air in question is not in issue.

The invention provides, for use in association with air conditioning equipment, whether of the kind incorporating air circulation apparatus, an air treatment element comprising a microbial treatment medium together with a supply of an entrainment or carrier medium therefor, such as water. In an physical embodiment, the provision of the entrainment medium, for example water, is conveniently in the form of a material, for example a polymer such as silicone or silicagel particles, which holds (volume for volume) large amounts of water and makes such available for use over a period of time by slow release of water. Other such water-holding polymers and the like are known to the competent technician in this field.

A practical embodiment of an air treatment element in accordance with this aspect of the invention provides the combination of a anti-microbial agent or a deodorant agent or an odourant agent, with a freezable or condensable supply of a treatment medium, such a treatment element being thus adapted to be frozen or condensed prior to use and adapted likewise to be employed as a temperature-reducing "ice-pack" which effects either microbial control, or odour control, or both, and can be packed into storage containers in association with stored goods in order to carry out these functions during transport and after.

Aspects and features of the invention are described in the priority application GB 9927617.2 filed on Nov. 24, 2000 and entitled "Biocide Air Delivery System" the entire text of which is incorporated herein by reference.

As described in GB 9927617.2, an aspect of the invention is a biocide air delivery system as follows.

1) This invention is a means of releasing a proven chemical anti-microbial agent in water vapour from a water saturated biocide/polymer mixture into the air stream of a fan or other forced air distribution system to achieve microbial control.
2) The purpose of the invention is to disinfect areas where micro-organisms may accumulate creating a health hazard and/or other deleterious effects.
3) The anti-microbial agent such as a proven biocide of the type developed as a preservative for medicinal application is blended with a highly absorbent polymer powder. The mixture is sealed in a porous or perforated sachet or container which can be stored in a dry place.
3) When saturated fresh water, water droplets will progressively filter through the sheets of the sachets; they are then drawn into the air stream by the action of the fan in biocide-laden water vapour.
4) One of the obvious applications of the invention is in air-conditioning systems where micro-organisms build up and cause discomfort for people in these environments.
5) Because the air-conditioning industry must conform to the basic business principle of minimum running costs, most of the systems use filtered air. A controlled balance of temperature and humidity must be achieved for a comfortable environment; when recirculated air is filtered and cooled or heated without sufficient import of additional fresh air it can cause dry respiratory passage, dry skin and hair, runny noses and general discomfort. Such operating conditions provide a suitable environment for the growth of micro-organisms which when caught in the air stream circulate around the buildings posing significant health risks, such as Sick Building Syndrome and Legionelloses.
6) Microbial growth is a common problem in air-conditioning and refrigeration systems. However, an air-conditioning system in a continuous cycle creates condensate water which will flow away through the drip trays and drains; research by the authors of the present invention shows that the condensate water normally produced by an equipment correctly maintained and running efficiently is in sufficient quantity to flush away the micro-organisms which may contaminate the system. But the tests also show that when the air-conditioning system does not function correctly, due perhaps to faulty valves or loss of refrigerant, less condensate water is produced which is therefore insufficient to flush away the micro-organisms providing them with innoculum for further growth and proliferation. A similar scenario occurs when the air-conditioning refrigeration cycle is interrupted, for example during periods of cooler weather when the system is shut down, or even for short period of time like week-ends. During those periods, little or no condensate water is produced and micro-organisms will settle and as soon as conditions are favourable, grow and multiply very quickly, when the air-conditioning system is operated, micro-organisms then quickly contaminate the building carried around by the air current.
7) For air-conditioning systems, refrigeration and associated equipment, the sachets containing the mixture of acrylate polymer powder and biocide powder are hydrated then positioned close to the fan held in a plastic vented holding grill or other device according to size and situations, designed to ensure maximum air-flow. The biocide laden vapour is drawn or expelled out of the sachets through the fabric and introduced into air-conditioning, normally inaccessible areas of the equipment and reduce the microbial build-up. The biocide laden water vapour then condenses onto the surfaces such as the evaporators continuously washing and disinfecting internal surfaces of such equipment.
8) As a useful addition to the operation, the sachets can be placed directly into drip trays and troughs receiving condensate water. The compound will soak in any fluid which may gather for example in situations when there is insufficient flow of water to wash away the microorganisms; the biocidal activities of the sachets will achieve microbial control.
9) Another application for the invention by the use of frozen hydrated sachet. The mixture of water saturated acrylate polymer and biocide can be frozen and kept frozen for periods of times exceeding that of ice; tests have shown that in a closed container, the temperature can be maintained at below 8 deg C for periods of over 36 hours.
10) This property can be used for the transport of temperature sensitive produce in portable container, in adverse conditions. Containers made of polystyrene or other acceptable material are fitted with perforated baffle plates at one or two centimeters inside the lid, the floor and the walls; behind the plates are inserted one or more layers of sachets containing an appropriate mixture of acrylate polymer and biocide powder. The containers are also fitted with one or several battery operated fans. During transport, the main fan can be connected to the 12/24 volt battery of the vehicle another fan being served by a 5/6 volt support cell battery. An example will be a box with dual axial fans, one powered by the transporting vehicle or its battery, the other being a fan of low voltage operated by a rechargeable portable battery; when the embodiment is disconnected from the main battery, the back-up battery cuts in to maintain continuity of the fan action with no interruption to the cooling operation inside the container. When the fans operate, they disperse the chilled water vapour emanating from the sachets within the container providing both cooling and microbial control functions. Refrigeration temperatures can therefore be sustained for one to two days before the frozen biocide sachets need replacing. By adding an extra layer of frozen sachets, test have shown that freezing temperatures can be maintained for 12 hours or longer with suitable insulation.

11) Chilled foods are usually distributed in containers such as plastic or polystyrene boxes by refrigerated lorries or vans. During deliveries when the van door remain open for unloading or loading, air at the ambient temperature enters the van which affects the produce stored in the vehicle. The invention will keep the temperature inside the containers within the acceptable limits of food hygiene as prescribed by the Health Authorities; the produce is packed at the refrigerated premises of the manufacturer or distributor in the chilled container where the invention is fitted; it is then loaded into the carrier's vehicles. The stored produce will not be affected by the opening of the vehicle's doors; it will allow the transit of the refrigerated container from vehicle to vehicle and consequently will enable the transporter to cover a much wider range of delivery over a much longer period.

12) Another useful advantage of the invention is that the water content of the polymer inside the sachets is progressively discharged through the fabric and by the action of the fan drawn as water vapour and spread throughout the container. This will maintain a constant degree of humidity which will keep the produce fresh. However any trace of liquid which may deposit inside the container will be absorbed by the super polymer to prevent the produce becoming wet. The combination of these functions will ensure that the produce maintains a pleasant and appealing appearance enhancing its presentation and commercial value.

13) The biocidal action of the invention will prevent possible cross contamination within the produce stored in the container during transport. The particular property of the polymer to absorb and contain contaminated liquids including oils, blood and other biological fluids, mixed with a biocide will facilitate the transport of temperature sensitive goods for medical purposes for example in areas and for applications remote from conventional refrigeration facilities, for relief operations or mobile medical services civil and military.

14) The invention can be used to deliver and introduce any chemical in vapour form into a forced air distribution system. Applications include the use of re-odorants to mask unpleasant and anti-social smells and the use of odour-releasing chemicals to enhance olfactory perception in commercial and recreational activities such as conference rooms, restaurants, leisure and sport centres, cinema complexes and similar areas where people gather.

15) An embodiment of the invention is now described by way of example with reference to the accompanying drawings in which:

FIG. 1 shows a sheet 1 of perforated sachets 2 containing a mixture of absorbent polymer and biocide 3.

FIG. 2 shows the sheet 1 of perforated saturated sachets enclosed in a 2 mm nylon sachet holder 4 placed opposite the fan 5 of an air conditioning unit, the said sachet holder being held in position with clips on the air inlet grill 6 showing the direction 7 of the air current which draws the biocide-laden water vapour inside the air conditioning system.

FIG. 3 illustrates the basic working parts of a typical air conditioning system showing the passage of the air current 7 drawn by the fan 5 carrying with it with biocide laden water vapour flowing through the air inlet grill 6, the evaporator with cooling coil 8 and dispersing through the air outlet 9. FIG. 3 also shows the condensate water dripping from the evaporator surface into the drip tray 10 and flushed through the drains 11.

16) The efficacy of the invention has been demonstrated through tests carried out in laboratories and in commercial/industrial premises. Some of the tests are reproduced in the following schedules:

TABLE 1

| | Aerobic bacteria per ml | | |
|---|---|---|---|
| | 0 h | 24 h | 120 h |
| Sample 1 + polymer | $6.45 \times 10^6$ | $5.95 \times 10^4$ | $6.30 \times 10^7$ |
| Sample 1 + polymer + biocide | $6.45 \times 10^6$ | 255 | $1.16 \times 10^4$ |
| Sample 2 + polymer | $1.92 \times 10^0$ | $1.52 \times 10^5$ | $4.10 \times 70^7$ |
| Sample 2 + polymer + biocide | $1.92 \times 10^0$ | 20 | $3.09 \times 10^1$ |

TABLE 2

| | Coliform bacteria per ml | | |
|---|---|---|---|
| | 0 h | 24 h | 120 h |
| Sample 1 + polymer | $>3.50 \times 10^4$ | $4.30 \times 10^6$ | $6.60 \times 10^6$ |
| Sample 1 + polymer + biocide | $>3.50 \times 10^4$ | $4.30 \times 10^6$ | <10 |
| Sample 2 + polymer | 1060 | 720 | $2.70 \times 10^5$ |
| Sample 2 + polymer + biocide | 1060 | <10 | <10 |

TABLE 3

| | *Escherichia coli* per 100 ml | | |
|---|---|---|---|
| | 0 h | 24 h | 120 h |
| Sample 1 + polymer | 65 | 87 | 311 |
| Sample 1 + polymer + biocide | 62 | <10 | <10 |
| Sample 2 + polymer | <10 | <10 | <10 |
| Sample 2 + polymer + biocide | <10 | <10 | <10 |

| Key | Tables 1–3 | |
|---|---|---|
| (i) | Sample 1 | contaminated water source was J-cloths from a small kitchen on an industrial site (serving 50 staff) |
| (ii) | Sample 2 | contaminated water source was "rinse water" from a commercial car wash |
| (iii) | polymer | Flexi-freeze sachets |
| (iv) | polymer + biocide | Sorbaban sachets |
| (v) | T.V.C.[5] | Yeast extract agar, pour plate method, 24 h at 37 deg C. |

TABLE 3-continued

| (iv) | coliforms/ E coli | Petri-film/Cololert: 2000 |

Note:
This test represents an extreme for the sachets, which are to be marketed to prevent indirect fluid-bourn contamination. Trial included:-
very contaminated water
high coliform/E. coli numbers
sachets were fully hydrated
sachets left at room temperature (18 deg C.)
important to note that counts increased in the non-biocide sachets!
All generic names are underlined

BRIEF DESCRIPTION OF THE DRAWINGS

Embodiments of the invention will now be described by way of example with reference to the accompanying drawings in which.

DETAILED DESCRIPTION

Figure 1:
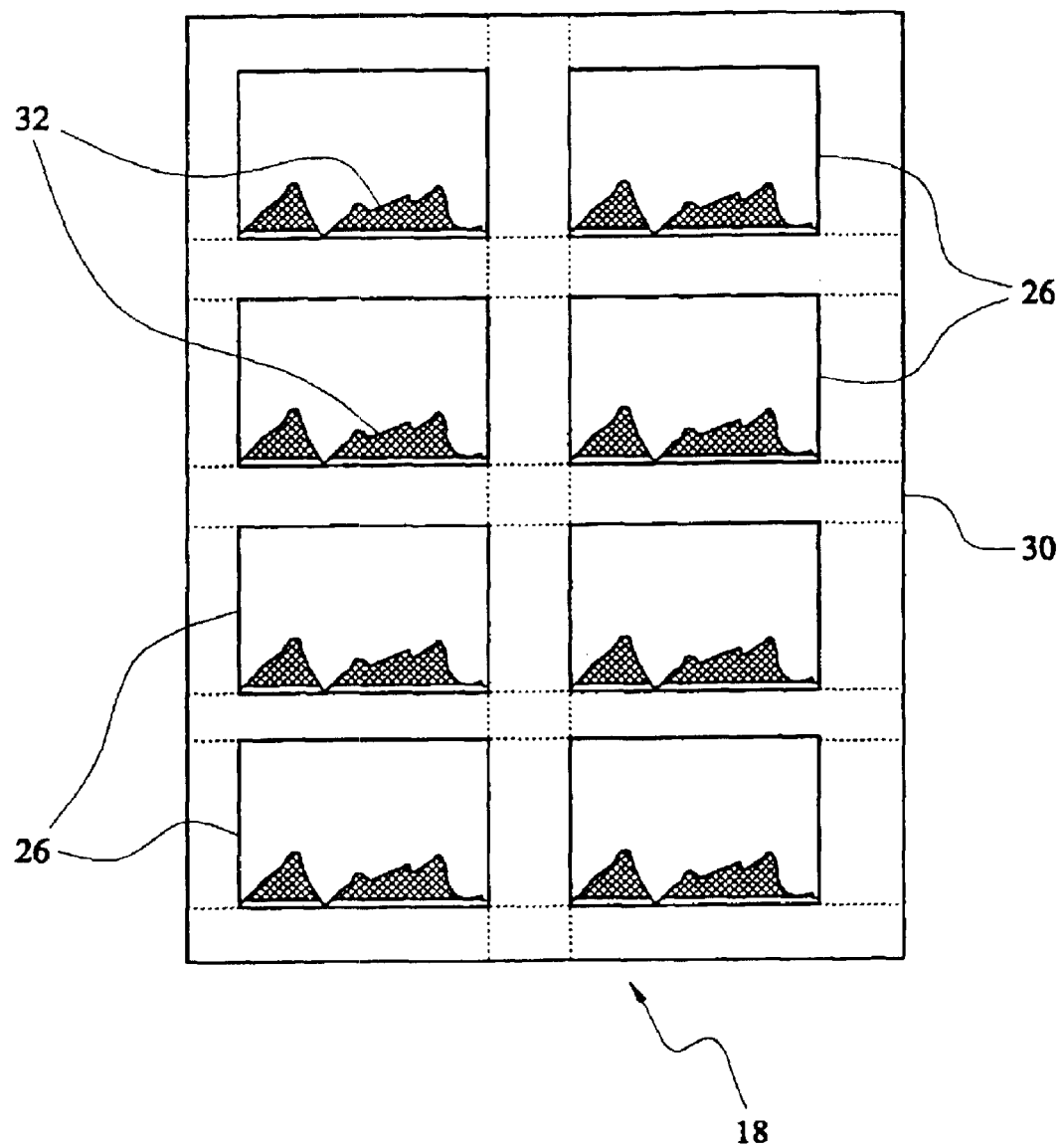
FIG. 1 shows a plan view of an air treatment element, in accordance with the invention, comprising an assembly of sachets.

As shown in the drawings, an air conditioning plant 10 comprises air-flow producing means in the form of a fan 12 and air-cooling means in the form of an evaporator 14, the evaporator 14 being positioned in the path of the air flow 16 from the fan 12.

An air treatment element 18 is positioned in the path of the in flow of air to the air cooling means and comprises a supply of a microbial control medium and a supply of an entrainment medium, the latter being adapted to enable the microbial control medium to be entrained therewith in the air flow 16 produced by the fan 12.

In use, the fan 12 entrains the microbial control medium with the entrainment medium from the air treatment element 18 in the air flow 16 and the air cooling means 14 cools the air flow as to cause some at least of the entrained microbial control medium to be condensed with its entrainment medium and removed from the air flow onto the cooled surfaces of the cooling means 14.

Figure 3:
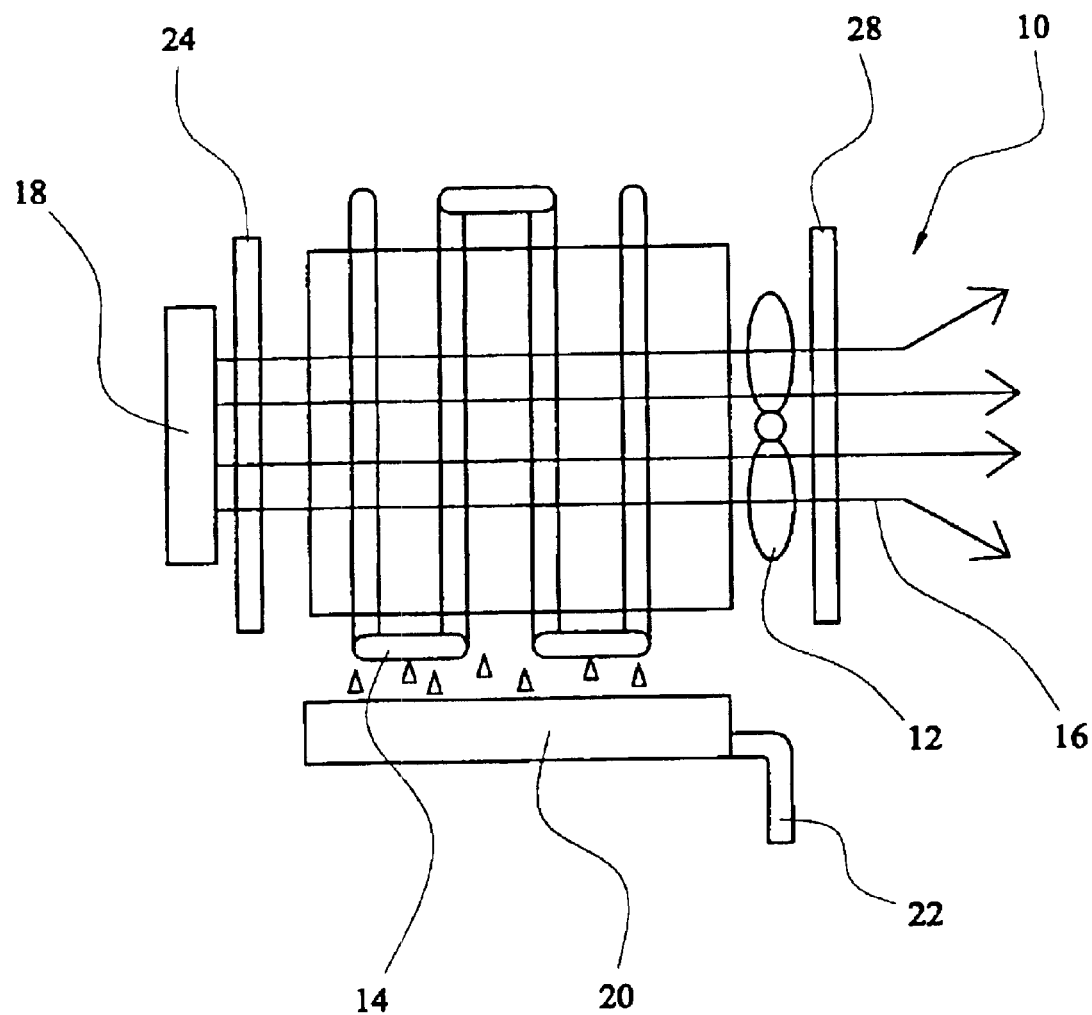
FIG. 3 shows the main hardware items of an air conditioning system incorporating the air treatment element.

There is shown in FIG. 3 the condensed entrainment medium (water) dripping from evaporator 14 into a drip tray 20 from which it is discharged via a drain 22.

Figure 2:
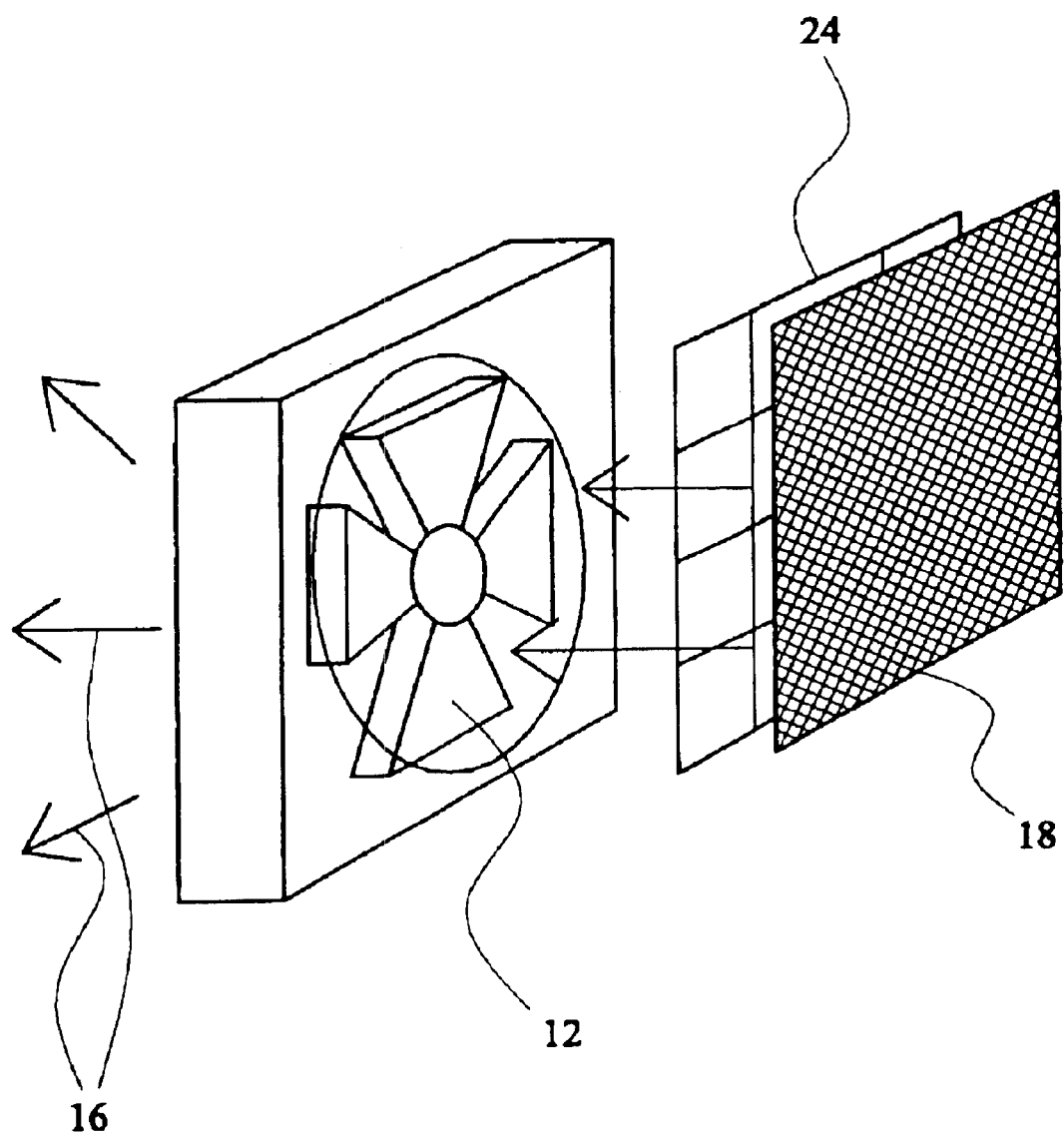
FIG. 2 shows the air treatment element of FIG. 1 mounted in a holder and placed in relation to the fan of air conditioning unit.

Air treatment element 18 is actually supported on an inlet grill 24 (which is shown separately in FIG. 3 for clarity of illustration). Grill 24 is perhaps best seen in FIG. 2 in relation to air treatment element 18 and fan 12.

The structure of the air treatment element 18 is best seen in FIG. 1 which shows an assembly of eight sachets 26 which are of a perforated structure comprising a biocide or microbial treatment medium together with an entrainment medium therefor which in this embodiment is provided by a water-absorbent polymer for example silicagel or like polymeric materials known to those technically competent in the field and capable of absorbing and releasing water to serve as the entrainment medium for the biocide or microbial treatment medium.

The structure of the sachets 26 is comparable to that of a tea bag in the sense that they are capable of containing the entrainment medium and the microbial treatment medium while admitting water and permitting a throughflow of air during use.

To prepare the air treatment 18 for use, it is immersed in a supply of sterilised water so that the water-absorbent polymer can become fully treated with water so as to hold the maximum content of the entrainment medium for subsequent cooperation with the biocide material and for entrainment of same in the air flow. After removal from the water bath, the assembly of sachets constituted by air treatment element 18 is mounted in relation to inlet grill 14 and fan 12 for use in the assembly shown in FIG. 3 as described above. Air passes through the sachets causing entrainment of the biocide material with the entrainment medium as described above.

Amongst other modifications which could be made in the above embodiments are the use of alternative entrainment mediums and alternative biocide materials. In the above embodiment, the biocide material may comprise the microbial treatment medium available under the trade mark BRONOPOL, which is available in a crystalline or powder format. Other biocides may be used.

The use of a water or other entrainment medium-releasing material such as a polymer enables the air treatment element to provide its function over a substantially longer period than would otherwise be the case if the sachets were merely wetted with water and effectively allowed to dry in the air stream.

In FIG. 3 an air outlet is indicated at 28.

In FIG. 1, sachets 26 are mounted on a support frame 30 in the dispositions shown and there is indicated within each sachets 26 the particulate material 32 of the microbial control medium and of the entrainment medium provided by the water-absorbent polymer.

What is claimed is:

1. A method of treatment of air conditioning systems of the kind comprising an air flow-producing device; and an air cooling device positioned in a path of air flow from said air flow-producing device; said method comprising the steps of:

a) applying a microbial control treatment medium to air contacting surfaces of said air cooling device, said step of applying said microbial control treatment medium comprising the step of providing an air treatment element positioned in a path of an in flow of air to said air cooling device and said air treatment element comprising a supply of said microbial control treatment medium and a supply of an entrainment medium therefor adapted to enable said microbial control treatment medium to be entrained therewith in the air flow produced by said air flow-producing device;

b) causing said air-flow producing means to entrain said microbial control treatment medium with the entrainment medium from said air treatment element in said air flow; and c) causing said air cooling device to cool said air flow to cause at least some of said entrained microbial control medium to be condensed and removed from said air flow onto cooled surfaces of said air cooling device.

2. A method according to claim 1 further comprising the steps of:

causing said air flow-producing means to continue to entrain said microbial control medium with said entrainment medium until said entrainment medium or said microbial control medium is exhausted, and then repeating the steps of said method after an interval of time.

3. A method of treatment of air conditioning and like systems comprising the steps of:
   providing an air treatment element positioned in a path of in flow of air and said air treatment elements comprising a supply of an air treatment medium and an entrainment medium therefor, and
   enabling said air treatment medium to be entrained with said entrainment medium in an air flow through said air treatment element.

4. An air treatment element comprising a supply of an air treatment medium and a supply of an entrainment medium therefor, wherein said entrainment medium comprises water.

5. An air treatment element comprising a supply of an air treatment medium and a supply of an entrainment medium therefor, wherein said air treatment medium comprises a fragrance medium and said entrainment medium therefor comprises an air-humidifying medium.

* * * * *